United States Patent
Greenfield et al.

(10) Patent No.: US 11,176,103 B2
(45) Date of Patent: Nov. 16, 2021

(54) SYSTEM AND METHOD FOR STORING AND ACCESSING DATA

(71) Applicant: PETAGENE LTD, Cambridge (GB)

(72) Inventors: Daniel Leo Greenfield, Cambridge (GB); Alban Rrustemi, Cambridge (GB)

(73) Assignee: PetaGene Ltd, Cambridge (GB)

( * ) Notice: Subject to any disclaimer, the term of this patent is extended or adjusted under 35 U.S.C. 154(b) by 314 days.

(21) Appl. No.: 15/730,432

(22) Filed: Oct. 11, 2017

(65) Prior Publication Data

US 2018/0101547 A1  Apr. 12, 2018

(30) Foreign Application Priority Data

Oct. 11, 2016 (GB) ...................................... 1617277

(51) Int. Cl.
*G06F 16/00* (2019.01)
*G06F 16/188* (2019.01)
(Continued)

(52) U.S. Cl.
CPC ........ *G06F 16/192* (2019.01); *G06F 16/2228* (2019.01); *G06F 16/278* (2019.01); *G16B 30/00* (2019.02); *G16B 30/20* (2019.02); *G16B 50/00* (2019.02); *G16B 50/30* (2019.02); *G16B 50/50* (2019.02)

(58) Field of Classification Search
CPC .. G06F 16/192; G06F 16/2228; G06F 16/278; G06F 16/188; G16B 50/00; G16B 30/00; G16B 99/00; G16B 50/30; G16B 50/50; G16B 30/20; H04L 67/1097
See application file for complete search history.

(56) References Cited

U.S. PATENT DOCUMENTS

2012/0310892 A1    12/2012   Dam et al.
2013/0204851 A1*   8/2013    Bhola ................. G06F 16/1744
                                                           707/693
(Continued)

FOREIGN PATENT DOCUMENTS

EP          2608096 A2       6/2013
WO          WO 00/14632 A1   3/2000
(Continued)

OTHER PUBLICATIONS

Deorowicz, Sebastian, and Szymon Grabowski. "Data compression for sequencing data." Algorithms for molecular biology : AMB vol. 8,1 25. Nov. 18, 2013, doi: 10.1186/1748-7188-8-25 (Year: 2013).*

(Continued)

*Primary Examiner* — Syed H Hasan
(74) *Attorney, Agent, or Firm* — Wolf, Greenfield & Sacks, P.C.

(57) ABSTRACT

A method of structuring data in a virtual file system, includes using the file system to apply specific handling of data that represents genomic sequence information or information that is related to genomic sequences. The method also concerns portioning the data into a collection of storage devices that have different cost and performance characteristics, wherein the splitting policy is based on a cost model. The method is executable by employing a computing device functioning under software control.

15 Claims, 6 Drawing Sheets

(51) Int. Cl.
  *G06F 16/27* (2019.01)
  *G06F 16/22* (2019.01)
  *G16B 30/00* (2019.01)
  *G16B 50/00* (2019.01)
  *G16B 50/30* (2019.01)
  *G16B 50/50* (2019.01)
  *G16B 30/20* (2019.01)

(56) References Cited

U.S. PATENT DOCUMENTS

| | | | | |
|---|---|---|---|---|
| 2014/0214333 | A1* | 7/2014 | Plattner | G16B 30/10 |
| | | | | 702/19 |
| 2014/0325587 | A1* | 10/2014 | Nilsson | H04W 12/02 |
| | | | | 726/1 |
| 2015/0227686 | A1* | 8/2015 | Sheinin | G16B 30/00 |
| | | | | 506/2 |
| 2015/0310228 | A1* | 10/2015 | Benz | G16B 45/00 |
| | | | | 726/26 |
| 2016/0248440 | A1* | 8/2016 | Greenfield | H03M 7/30 |
| 2016/0306922 | A1* | 10/2016 | van Rooyen | H04L 67/10 |
| 2018/0068000 | A1* | 3/2018 | Messaoud | G16B 20/00 |
| 2018/0089224 | A1* | 3/2018 | Muthuswamy | H04L 67/06 |
| 2018/0152535 | A1* | 5/2018 | Sade | G16B 30/00 |
| 2019/0304571 | A1* | 10/2019 | Vakili | G16B 50/30 |

FOREIGN PATENT DOCUMENTS

| | | | |
|---|---|---|---|
| WO | 2014/036167 | A1 | 3/2014 |
| WO | 2016/185459 | A1 | 11/2016 |

OTHER PUBLICATIONS

Ochoa-Alvarez, Idoia. "Genomic Data Compression and Processing: Theory, Models, Algorithms, and Experiments." In SearchWorks Catalog, searchworks.stanford.edu/view/11849275. (Year: 2016).*
Rodrigo Canovas, Alistair Moffat, Andrew Turpin, CSAM: Compressed SAM format, Bioinformatics, vol. 32, Issue 24, Dec. 15, 2016, pp. 3709-3716, https://doi.org/10.1093/bioinformatics/btw543 (Year: 2016).*
Bonfield JK, Mahoney MV Compression of FASTQ and SAM Format Sequencing Data. PLOS ONE 8(3): e59190. https://doi.org/10.1371/journal.pone.0059190 (Year: 2013).*
Search Report under Section 17(5) received for United Kingdom Patent Application No. GB1617277 7, dated Mar. 23, 2017, 4 pages.
Haussler, David, et al., "A Million Cancer Genome Warehouse", Electrical Engineering and Computer Sciences University of California at Berkeley, Nov. 20, 2012, pp. 1-59.
Vrable, Michael, et al., "BlueSky: A Cloud-Backed File System for the Enterprise", usenix, 10th Conference on File and Storage Technologies, Feb. 14-17, 2012, 14 pages.
Fritz, Markus Hsi-Yang, et al., "Efficient storage of high throughput DNA sequencing data using reference-based compression". Method, Genome Research, vol. 21, No. 05, May 1, 2011, pp. 734-740.
Tang, Yang, et al., "GRANDET: A Unified, Economical Object Store for Web Applications", Proceedings of the Seventh ACM Symposium on Cloud Computing, Oct. 5-7, 2016, pp. 196-209.
Cock, Peter J. A., et al., "The Sanger FASTQ file format for sequences with quality scores, and the Solexa/Illumina FASTQ variants", Survey and Summary, Nucleic Acids Research, vol. 38, No. 06, Dec. 16, 2009, pp. 1767-1771.
Raghavan, Ajaykrishna, et al., "Tiera: Towards Flexible Multi-Tiered Cloud Storage Instances", Proceedings of the 15th International Middleware Conference. ACM, Jan. 13, 2014, 12 pages.
Extended European Search Report for European Application No. 17020466.3 dated Feb. 26, 2018.
Gardner et al., Parallel genomic sequence-searching on an ad-hoc grid: experiences, lessons learned, and implications. Proceedings of the 2006 ACM/IEEE conference on Supercomputing Nov. 11, 2006:14 pages.

* cited by examiner

SYSTEM AND METHOD FOR STORING AND ACCESSING DATA

CROSS-REFERENCE TO RELATED APPLICATIONS

This application claims the benefit under 35 U.S.C. § 119 of United Kingdom Patent Application No. GB 1617277.7, filed Oct. 11, 2016, and titled "SYSTEM AND METHOD FOR STORING AND ACCESSING DATA," which is incorporated by reference herein in its entirety.

TECHNICAL FIELD

The present disclosure relates to systems that are specialised in storing data that represent genomic sequence information or data that represent information that is related to genomic sequences. Moreover, the present disclosure concerns methods for storing such data across multiple storage components according to access demand and access patterns. Furthermore, the present disclosure concerns methods for representing the same data in different file formats. The present disclosure also relates to software products recorded on machine readable data storage media, wherein the software products are executable on computing hardware for implementing aforesaid methods.

BACKGROUND

Over the past decade, rapid advances in sequencing technology have resulted in a reduction of the cost of sequencing a given human genome by a factor of 10,000. Resulting rapidly growing genomics data volumes pose enormous challenges in terms of data storage cost and computational efficiency. It is especially challenging that storage costs are growing exponentially relative to sequencing costs.

Modern high throughput sequencers (also known as Next-Gen sequencers) generate large amounts of raw genomic sequence data. Due to imperfections in the process of sequencing, small parts of the DNA molecule are sequenced (read) multiple times in order to increase the confidence on the information acquired (i.e. increase signal strength by aggregation). The sequencer produces information for all these reads, where each read represents not only the sequence of DNA bases, but also the corresponding quality score information as well as other supporting information. Normally, the data output from the sequencer is stored in a FASTQ™ (or FASTA™) data format. The information generated by the sequencer often needs to go through a number processing stages (e.g. alignment of reads) before it is used by bioinformaticians and other researchers. The most common formats that are used for sequence alignments are BAM, SAM and CRAM. For a human genome, these files often range between 100 GiB and 1 TiB.

Existing storage systems and file-systems do not have any specific handling or consideration towards the internals of genomics datasets and the files where this data is stored; in other words, such existing storage systems are not specifically tailored to the needs and data structures of genomics datasets. An unsuitability of the existing storage systems is a technical problem that can result in unnecessary large data processing capacity needing to be employed, as well as slower data access and data searching than would ideally be desired by aforementioned bioinformaticians and other researchers. Data access speed and data processing efficiency are both technical issues that computer systems designers are often required to resolve.

Therefore, there exists a need for more efficient methods and more efficient systems that have consideration towards genomics dataset internals, namely are configured to handle and process genomics datasets in a more efficient manner.

SUMMARY

The present disclosure seeks to provide an improved method of organising (namely, providing, processing, transferring, searching, reformatting) data across various data storage systems, wherein at least some of the data storage systems are mutually different.

Moreover, the present disclosure also seeks to provide a system that is configured to separates operations of organising data from operations of presenting data.

According to a first aspect of the present disclosure, there is provided a method of providing data by utilising a virtual file system, wherein the data represents genome sequence information or information related to genome sequences, wherein the virtual file system includes a front-end and a back-end, characterized in that the method includes:
(i) presenting the data into one or more file formats to the front-end of the virtual file-system; and
(ii) recording the data in one or more machine readable data storage media of the back-end of the virtual file-system, wherein the data when stored is structured in a different file format in comparison to the one or more file formats used in the front-end of the virtual file-system.

The invention is of advantage in that arranging for the front-end of the virtual file-system to reformat data to suit more optimally a data storage structure of the data storage media improves technical operating performance of a data processing system that is arranged to employ the method.

According to a second aspect of the present disclosure, provided is a method of operating a data processing system, wherein the method includes arranging for the data processing system to portion data and to record the portioned data in a plurality of machine readable data storage media, wherein the data represents genome sequence information or information related to genome sequences, characterized in that the method comprises:
(i) portioning the data into a plurality of data portions according to a cost model that utilises genomic attributes;
(ii) assigning each portion into one or more of the plurality of machine readable data storage media; and
(iii) recording the data portions into each assigned machine readable data storage media.

A Virtual File System (VFS) that is capable of handling genomic datasets in a specialised way can result in a more cost effective data processing system and enable faster dataset analysis to be formed using the data processing system. Beneficially, when arranging for the data processing system to implement the VFS, the data processing system is configured, namely is operable, to auto-decompose and reconstitute the genomic data in a just-in-time manner for improved data storage cost and processing efficiency. The genomic data can be potentially stored losslessly in any format, but accessed with a manner that has improved performance and cost associated with the most efficient lossy file formats.

Optionally, in the step (ii), the method includes compressing the data portions.

Optionally, the method includes using a virtual file system that includes a front-end and a back-end, wherein the method includes:

(i) presenting the data in one or more file formats to the front-end of the virtual file-system; and (ii) recording the data in one or more machine readable data storage media of the back-end of the virtual file-system, wherein the data when stored is structured in a different file format in comparison to the one or more file formats used in the front-end of the virtual file-system.

Optionally, when portioning of the data into a plurality of data portions, the method includes splitting quality scores of the genome sequence information into two or more of the data portions. More optionally, the method includes portioning the data into a plurality of data portions, wherein the portioning comprises splitting tag fields of the genome sequence information into two or more of the data portions. Additionally optionally, the data portions include a primary portion and a secondary portion, wherein the method includes accessing the secondary portion less frequently than the primary portion.

Optionally, the method includes assembling a data fragment from data that is portioned, wherein the data is read from the plurality of machine readable data storage media, wherein the method comprises:

(iv) determining a set of machine readable data storage media where the data portion is recorded;

(v) reading data portions from each of the set of machine readable data storage media; and (vi) assembling the data fragment from the data portions.

Optionally, the method is implemented using a computing device for storing and portioning data.

According to a third aspect of the present disclosure, provided is a computing device operating under software control for implementing the methods of the first aspect and/or the second aspect.

According to a third aspect of the present disclosure, provided is a computer program product comprising a non-transitory computer-readable storage medium having computer-readable instructions stored thereon, the computer-readable instructions being executable by a computerized device comprising processing hardware to execute the methods of the first aspect and/or the second aspect.

DESCRIPTION OF THE DIAGRAMS

Embodiments of the present disclosure will now be described, by way of example only, with reference to the following diagrams wherein.

DETAILED DESCRIPTION OF EMBODIMENTS

Figure 1A:
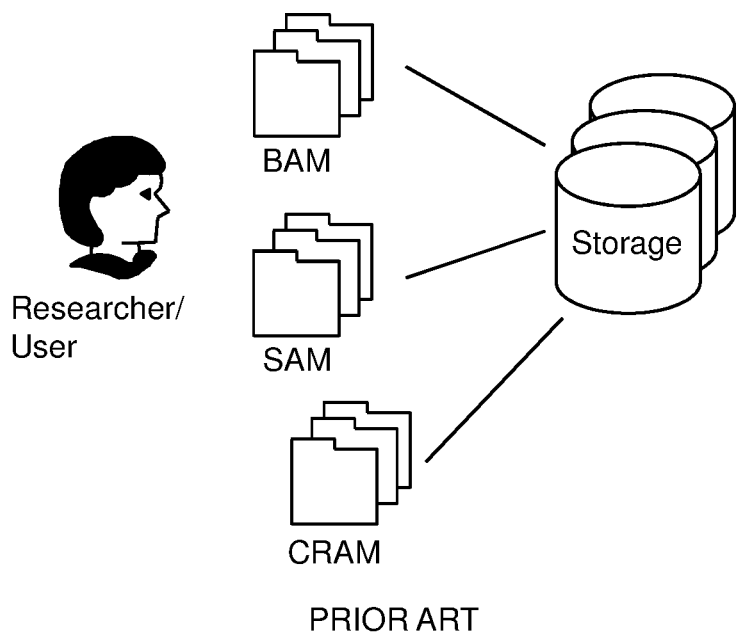
FIG. 1A is a schematic illustrating access to genomics data in known existing storage systems.

In an embodiment, genomics data is stored and accessed using a Virtual File System (VFS). There is thereby achieved special handling of specific data through a Virtual File System that brings many advantages:

1. There is enabled a separation of handling the storage of data in a backend (of a VFS) from a handling of a representation of the data in a frontend (of the VFS). The data in the backend can be stored using specialised compression algorithms without affecting the way users access the data in the front-end (namely, users still access the data in the same file formats that they are used to). Referring to FIG. 1B, more details of such a manner of operation are shown; there is shown a data processing system, wherein "just-in-time" reconstitution (of data) is performed whenever a given file is accessed in any of the formats supported on the frontend.

2. For reducing storage capacity requirements, whenever appropriate, the VFS can store genomics data in a compressed format with reference to a dedicated genome (namely, a reference genome). For example, newly added gene sequences in formats such as SAM and BAM can be compressed using a reference genome to a CRAM format, or some other reference-based format.

3. For reduced data storage costs or higher performance (or both), the genomics data in the backend can be split into different files/object and distributed across different tiers of storage according to a model that incorporates cost of access, performance, and importance of each split portion. Genomic attributes such as sequence data, quality scores, tags in formats such as BAM/SAM/CRAM, as well as any available metadata beneficially contribute on how genomics data is split into portions. The given model determines the storage tier where the given split portion would be stored. For example, the data portions that are more frequently accessed can be stored as files/objects in faster (and usually more expensive) storage tiers for better performance (for example, solid state data storage devices, SSD). On the other hand, other data portions that are accessed less frequently can be stored as files/objects in a slower storage tier that have lower running costs. Alternatively the genomics data can be split into files/objects according to importance and stored on a single tier but whereby caching will implicitly (based on access patterns) store a copy of important splits in faster storage (for example, in data memory or SSD) while leaving the unimportant splits in slower storage (the single main storage tier). Such splitting results in a performance improvement compared to unsplit data since caching cannot separately cache the important unsplit data whilst not also caching the unimportant unsplit data. Overall, in respect of operation of the data processing system, this leads to better cache utilisation, and lower I/O demands for the underlying storage tier(s). In a cloud environment, such as on Amazon AWS (Amazon Web Services), there are a plurality of storage tiers available, such as SSD elastic block storage, HDD elastic block storage, as well as fast object storage (S3), infrequently accessed object storage (IAS) and cold object storage (Glacier). Ultimately, within a cloud datacentre, these different tiers of storage are still contemporarily implemented as regular physical storage such as in the form of hard disks, flash, optical disks and tape. For an on-premises system the local tiers of available storage (e.g. such as local disk, object storage and tape) may also be augmented with additional cloud storage, such as from Amazon AWS (for example, S3, IAS and Glacier), wherein these names are trade marks. Furthermore, there has been a long history of tiered storage implementation that automatically migrate data from one storage tier to another, typically according to usage, so as to reduce overall cost, balanced with maintaining storage performance goals. Various examples of tiered storage are known including local tiered storage, cloud-augmented tiered storage, and distributed tiered storage with or without automatic migration.

4. According to the present disclosure, a given VFS user is able to access the genomics data in standard file-formats. Moreover, the VFS frontend can represent a same given genomics data in different file-formats. Storage overheads for supporting additional representations are typically negligible. For example, a human genome can be represented by just-in-time conversion in BAM, SAM and CRAM on the frontend. On the backend, the same file can be stored in a different format that allows better compression or enables splitting of the data that represents the file across different storage tiers.

5. In many types of data analysis and processing that are performed on genomics datasets, only a small subset of the data (genome region) is required. Efficient lookup and access to specific portions of the dataset can be transparently supported in this VFS framework by indexing the dataset accordingly. Moreover, a dedicated virtual directory tree can be used to access portions of this data. For example, for a BAM file that contains a human genome, the virtual directory tree would first represent each chromosome in a separate directory and then the genome contents of each chromosome would be further split up across several directories that would represent views of specific regions (slices) within the genome (see FIG. 2 for more details). For more efficient access, the data that represents the genome in the backend can be split into smaller files. This splitting of the genome data into smaller files can be done according to regions (slices) in order to better correspond with front end views of regions/slices. In overall, these small files can improve cache utilisation.

6. Since the VFS mounts in this system represent virtualised views of genomics data, files and directories that represent this data in the frontend are virtual and therefore there is a lot of flexibility in the directory structure and namings of files and directories. The VFS not only can support virtual directories to represent containers for specific file-formats (for example, dedicated directories for different file formats—BAM, SAM and CRAM), but it can also include virtual directories that encode access patterns (for example, virtual directory BAM-p64k could be used to indicate that any access of files within this directory will result in a pre-fetch of 64 kB blocks).

7. If the VFS is used from the command line tool or a path is explicitly specified, virtual directories that are not represented (explicitly visible) during ordinary directory traversal can be implicitly accessed. In other words, the directory could be instantly created upon a request to access it (in a just-in-time manner). This would allow custom prefetching and efficient access to custom regions of the genome. For example, a file path such as this: /mnt/bam/p128k/chr1/12500-16000/HG00096.bam although is not present in the fixed directory structure, can still be accessed and will include a portion of chromosome 1 of genome HG00096.bam, where the start position of the genome in 1-based coordinates is 12500 and the end position is 16000. Moreover, access to this portion of the genome would use 128 kB prefetching (due to the presence and encoding of string 'p128k' in the given file path).

8. Since the VFS understands the internals of genomic files/datasets, it also understands the meta-data and other tags internal to genome datasets, and can automatically build virtual directory trees according to this meta-data or other tags. For example, upon adding the first chimpanzee genome, the VFS can note that it is a new species in the dataset and automatically add an explicit chimpanzee sub-directory that groups together all chimpanzee genomes. Moreover instead of explicit subdirectories, search queries can be constructed as implicit just-in-time subdirectories as well. For example instead of the VFS explicitly constructing a chimpanzee subdirectory view as soon as a chimpanzee genome is added, the user may navigate to an empty species directory and then enter a non-existent chimpanzee subdirectory. This would inform the VFS to implicitly construct a just-in-time chimpanzee subdirectory with the contents corresponding to a search query of "genomes tagged as being of species chimpanzee".

9. Many types of analysis and processing that are conducted in genomics datasets often involve the same genome region for multiple instances of genomes. The VFS in the backend can optionally group regions of multiple genomes together so that they can be accessed more efficiently.

10. Genomics data (for example, files stored in SAM/BAM and CRAM format) contain many different types of information that are structured into different types/attributes/tags. These different data categories can be grouped together for more efficient access. Moreover, the data from the same category (type) can be encoded and compressed more efficiently since the compression algorithms can be chosen specific for that data category (type) rather than using one general compression algorithm on mixed types. Although this is not possible with existing genomic file formats, the VFS framework allows such targeted compression on the back-end, irrespective of front-end file formats.

11. Processing of genomics data in a data processing system is mostly characterised by write-once/read-multiple times access pattern (followed by an optional, eventual delete, when data is not required anymore). The data that represents the genome is immutable (namely, it does not get modified in the meantime). The VFS can be built with this assumption of immutability, which allows more efficient distributed caching of this data, since changes to a file do not invalidate the cached storage of underlying immutable data. For example, on a cluster environment, the VFS instance on each node (machine) can read a file from shared or distributed storage and can assume that the file will not be modified by another node. This allows it store the file in cache and reuse it multiple times without checking another node or shared storage for whether or not it has been modified in between uses. It also means that it does not need to invalidate the cache content, or lock the content on the storage medium to prevent it from being modified. This immutability of back-end files/objects thus speeds up and simplifies their caching.

12. In the data processing system, use of the VFS framework inherently allows backwards compatibility without compromising on any forward efficiency gains that can be made. The separation of the frontend from the underlying backend storage allows further technological improvements to be made on either side. Various access methods (pursuant to the present disclosure) and file formats can be supported on the front end, while still presenting multiple backwards-compatible views of the same dataset (in order to support old and existing toolchains). On the backend side, various improvements in compression algorithms can result in further reduction of storage capacity requirements and various intelligent caching methods are susceptible to result in better access performance when accessing data. These improvements are optionally integrated at a future date by using a plug-in architecture. A plugin architecture also allows third-party developers to add functionality, such as support for new front-end file formats (just-in-time converting to and from backend file formats), and additions to the virtual directory structure. The VFS serves as an abstraction platform for third-party developers to incorporate new genomics technologies.

13. Just as multiple front-end views of the back-end data can be presented as part of the Virtual File System, so too can multiple-front end API accesses also be made available by using an API-bridge. The API-bridge converts API calls on the front-end of the API to equivalent commands on the back-end, the response of which is converted back. For example API-access can be added for a Hadoop-compatible bridge, HDFS access API, or Spark API for ADAM support. The standard plugin architecture can enable new third-party API front-ends to be added to bridge to the VFS, or the back-end (or both), in addition to plugins for new virtual files/directories within the VFS.

Since the backend of the VFS can be structured separately from the frontend, further optimisations can be added in order to improve cost effectiveness as well as performance of a system that stores and analyses genomics datasets.

Splitting Genomics Data Across Different Tiers

In general—a smaller amount of commonly used data portions (core) can be stored on faster, more expensive, data storage, whereas bulkier less frequently used data portions (non-core) can be stored on slower, cheaper data storage media(s) according to need. This is separate from the categorisation of 'hot data' vs 'cold data' whereby files are stored according to frequency/access patterns. In this framework, the internals of genomics files are analysed, split up and reconstituted, as opposed to (hot/cold) techniques that operate on opaque data. This also improves network traffic and caching performance by not requiring the transfer or caching of the bulky non-core portion of the data when only core data is needed.

Splitting Quality Score Information

As referred above, for reducing storage costs the genomics data in the backend can be split across a plurality of tiers, for example different tiers, of data storage according to its importance. Quality score information constitutes the majority of the data in gene sequence information that is produced by high throughput sequencing. A quantised version of quality score information is sufficient for many types of analysis. This lossy version of compression can result in much higher compression rates compared to lossless version. For other analysis where the full fidelity is required (namely, lossless analysis), the remainder of quality score information (the arithmetic difference of the quantised version and the original version of the same information) can be compressed and stored separately. This scheme saves two versions of quality score information 1. the quantised/lossy version, that benefits from good compression rates and due to its relatively small size can be stored in faster data storage;
2. the remainder part (delta), that can be used together with the quantised version to restore the original quality score information. This part is accessed infrequently and constitutes the majority of the compressed data. Given the infrequent access, it is moved to a different storage medium that is more cost-effective. Alternatively the full version of the quality score information can be saved to the more cost-effective storage medium—resulting in a higher storage cost than if only the remainder (delta) part is stored, but resulting in a full backup/copy in that storage medium that can be accessed without requiring the lossy/quantised version for reconstruction.

Splitting Separate Categories of Data (Tags)

Fields such as rarely used tags (for example, BQ:Z) are also split and stored separately (into different files potentially on different tiers of storage). This thus comprises a more 'columnar' storage of the data fields that can be split to media with different cost and performance characteristics according to the importance of the data.

Implicit Tiering

The tiering referred to in the present disclosure covers both explicit tiering, whereby data is explicitly stored on different storage devices according to their cost/performance characteristics, as well as implicit tiering whereby data is automatically moved onto different storage devices according to their cost/performance characteristics and access patterns. Caching, whether in memory, or in SSDs, or other storage tier, is a form of implicit tiering that seeks to improve performance while minimising I/O costs. However, caching operates on opaque files and is not intelligent enough to determine what content within files (especially interleaved/mixed content) is needed and what is not needed. Thus, by splitting genomics data according to type and region into separate files, the techniques described here allow caching to operate separately on these types of content and automatically move this split data into different implicit tiers according to access pattern, and thus optimise storage. For example, this enables the quantised/lossy split data to move to cache while leaving behind the delta component on non-cached storage. Because there is less data that effectively needs to be commonly accessed, this results in a performance improvement due to better cache utilisation compared to not splitting the data in this manner. Thus implicit tiering can occur even when using a single back-end storage device due to caching.

Reconstituting Split Data at the VFS Frontend

According to the virtual directory structure, the genomics data stored in the backend can be reconstituted to any number of file formats (e.g. SAM, BAM, CRAM, etc. . . . ) as uncompressed and compressed versions, and according to how much non-core data to include. These virtual directories can include other subdirectories to specify how much non-core data to access. For example, a subdirectory can be named bam-core, where only core data is accessed in BAM format; bam-bqz, where core data as well as BQ:Z data (that is part of non-core data) is included; bam-fullqs, where bam files are accessed with full-fidelity quality scores, etc. Based on the data requests made on the front end, the back-end can automatically reconstitute the required front-end data from the (multiple) back-end splits. For example, for the bam-core version, only one of the data splits may be needed, whereas for the bam-fullqs version data may be read from two splits of the data and be combined to reconstitute the full-fidelity quality score, and for the bam-bqz, data may be read from further splits and combined to reconstitute the required virtual file(s). Furthermore, as the data is split both according to type (fidelity of quality score, unneeded tags, etc.) and according to region (chromosome and spans), reads of larger regions may involve combining multiple region splits as well as combining multiple type splits. In this manner, the user can specify the desired characteristics of genomic data as a path to a virtual directory and the files located at that path will transparently adhere to those characteristics, reconstituted as needed from across one or more files on one or more back-end data storage devices.

Structuring Backend Data to Optimise Specific Access Patterns

The VFS can be configured to optionally store the core data in a different layout that is optimised for a particular access pattern. For example, if it is known that multiple genome samples are likely to be accessed together (according to the genome position) then the backend data that corresponds to the same genome position across multiple samples can be stored in the same region of the storage backend. For example, instead of storing on disk genome A,B,C,D region 1, 2, 3, 4 as A1, A2, A3, A4, B1, B2, B3, B4, C1, C2, C3, C4, D1, D2, D3, D4, an alternative storage layout can be chosen: A1, B1, C1, D1, A2, B2, C2, D2, A3, B3, C3, D3, A4, B4, C4, D4 if it is known that A, B, C and D are likely to be accessed together at the same positions. In overall, the data can be stored in multiple different layouts to accommodate multiple different access patterns. Since the core data is significantly smaller when compared to the original data, saving it in multiple layouts will not incur significant storage overheads. The genomes that are stored together in this manner could be clustered according to phylogeny (or trio), or by phenotype, or by some other relational category.

A Virtual File System Customised for Genomics Applications

Writing Data to the File-System

Figure 5:
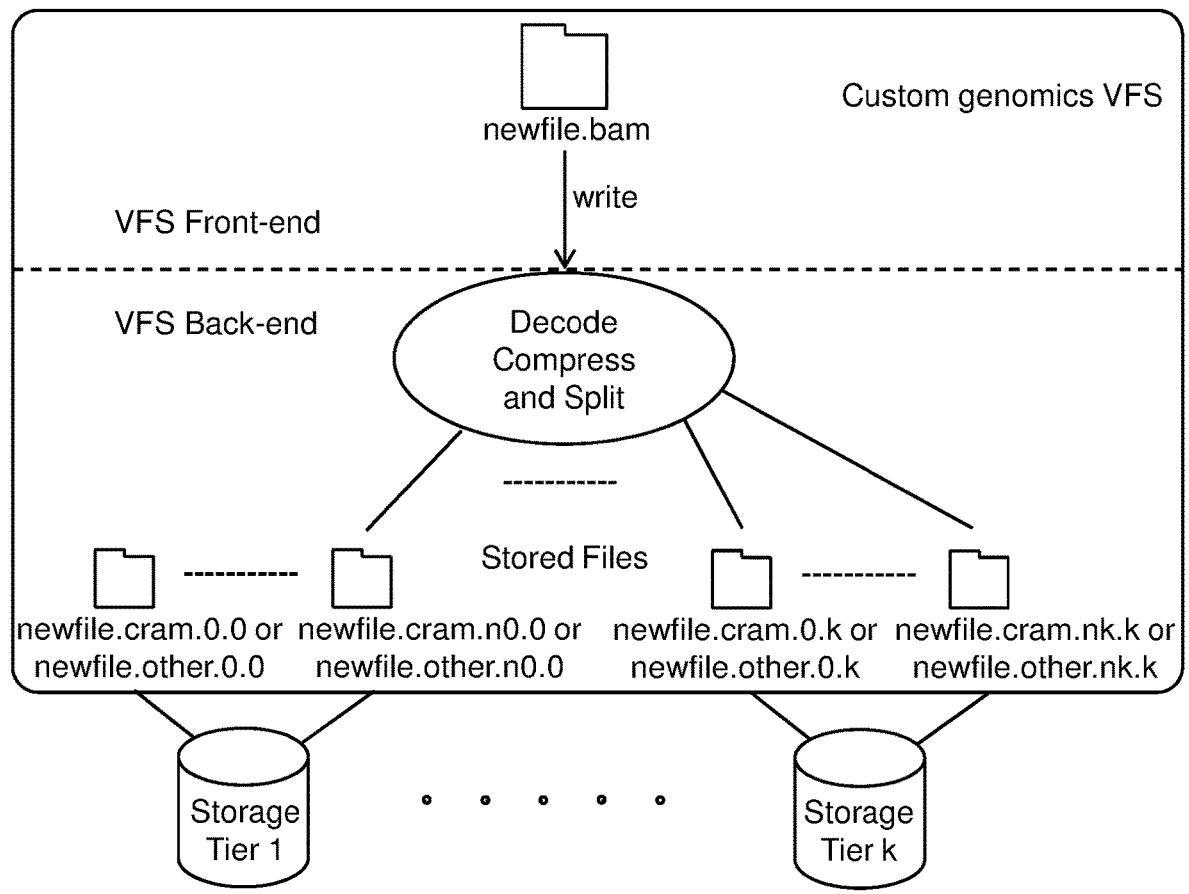
FIG. 5 is a schematic illustration of the method of writing on the VFS.

The genomics data can be written into any one of the supported front-end formats. Each supported format may include an encoder and a decoder for the format; the encoder and decoder are optionally software implemented or hardware implemented, or a combination of software-implemented and hardware implemented. Optionally, the encoder and decoder are dynamically reconfigurable to employ various encoding and decoding algorithms that are adapted (namely optimized) to encode specific types of data structure. These encoder and decoder, namely modules, enable encoding and decoding of specific data formats from/to the common backend VFS format. Once the data is decoded, the process of compression and splitting the data across different tiers can follow. More details are illustrated in FIG. 5. The process of decoding, compressing and splitting may be done inline (namely, while the file is being written) or it can be done through a post-processing routine (namely, the file is written to a temporary location and then the process of decoding, splitting and compression follow). The written file can also be indexed in order to make access to portions of content more efficient.

Reading Data from the File-System

Figure 6:
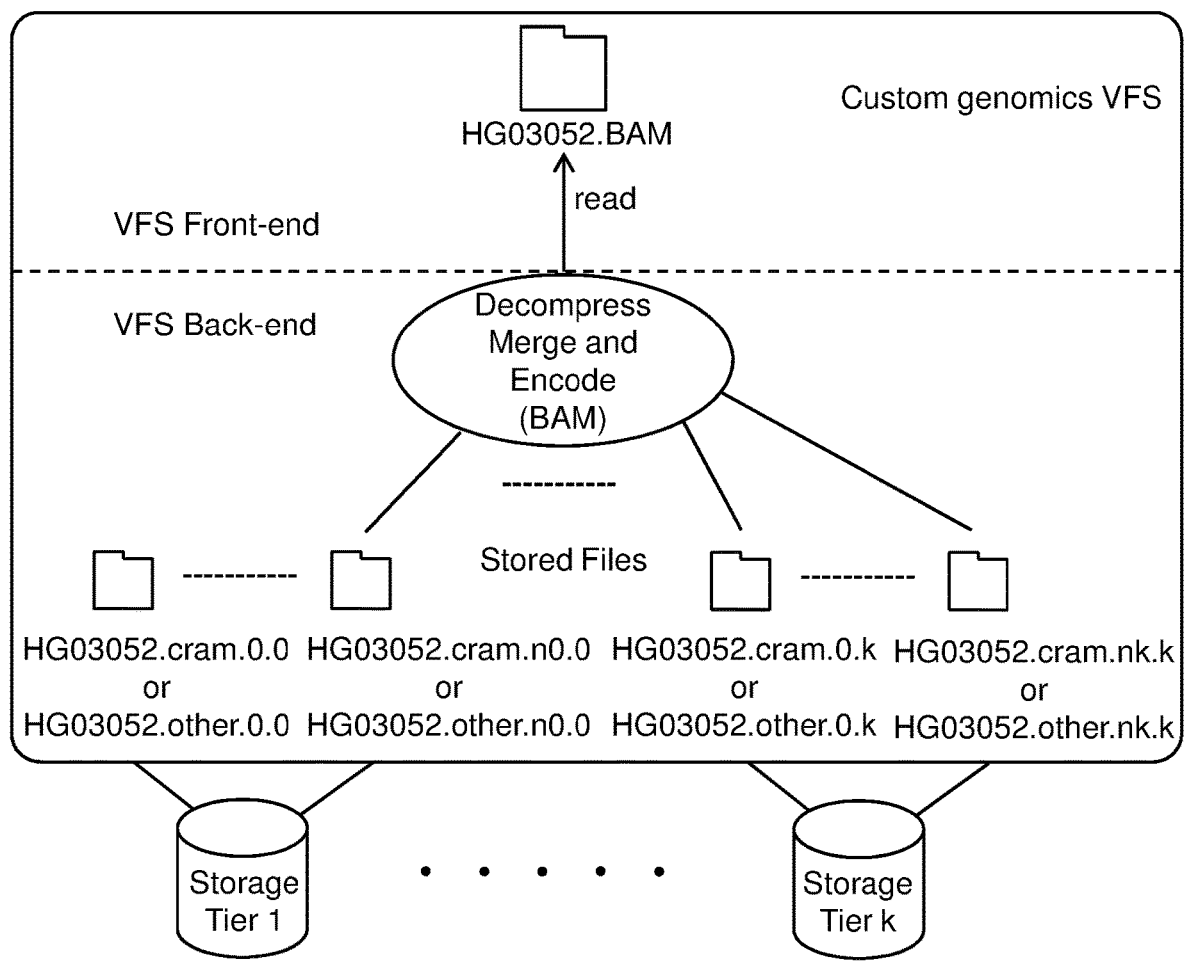
FIG. 6 is a schematic illustration of a method of reading from the VFS.

The VFS will represent genomics data stored in a backend in all the available front-end formats. The files represented through the VFS are virtual. The VFS will first determine the storage tier where the underlying data is stored (or the optimal storage tier if the data is stored in multiple tiers). Once the underlying data files are loaded, decompressing and merging will follow before the data can be encoded into the front-end format. More details are illustrated in FIG. 6. The VFS may consult indexing information that may be available in the backend in order to efficiently determine the location of the data that is being read.

Examples of Virtual File System Mechanisms

Virtual File Systems can work through a number of mechanisms in an Operating System, for example an Operating System of a data processing system. Without limitation, this can include:

(i) kernel file-system drivers;

(ii) a user-mode file system (such via as the Linux Filesystem in Userspace, otherwise known as FUSE); and/or (iii) via a shim library access layer such as by intercepting filesystem accesses via the LD_PRELOAD mechanism on Linux.

Example Workflow

In an example situation wherein the Virtual File System is mounted and available to a use, a given user copies a BAM file to the file-system. The BAM file is automatically stored in a back-end format, where the content is reference-based (for example, CRAM) compressed and split into two types (namely, core and non-core), and segmented further according to genome position. The corresponding underlying files are then stored in directories located on two tiers of data storage, namely disk storage for core data, and tape or optical storage for non-core data (this storage could comprise disk-based caching on top of it). The non-core data from the BAM file is first written to this tape/optical cache which is gradually flushed out to the tape/optical system.

The given user navigates to a lossy access directory under the VFS, and then a SAM sub-directory, then to a chromosome 11 subdirectory. Here, the user can access the virtual SAM file corresponding to chromosome 11 of this BAM file. This is a lossy instance that is accessed and so the VFS accesses the core data and does not access the non-core data to reconstitute the SAM file. It also accesses the corresponding sequence reference file in order to reconstitute the SAM file. The user then navigates to the lossless access directory under the VFS, and then to the BAM sub-directory, then to chromosome 10. The virtual BAM file here is reconstructed by the VFS using both the main core and the non-core data. This access may result in data retrieval into tape/optical cache from tape/optical storage if necessary. Next the user starts a distributed cluster compute job where the source data points to a VFS directory corresponding to lossy BAM-based data in the virtual pos1000sam100/access subdirectory. This access directory informs the VFS that accesses will likely occur 1000-base positions at a time iterating across 100 samples before moving onto the next 1000-base position. The underlying VFS will perform data caching and prefetching in order to optimise for this access pattern.

DETAILED DESCRIPTION OF FIGURES

Figure 1B:
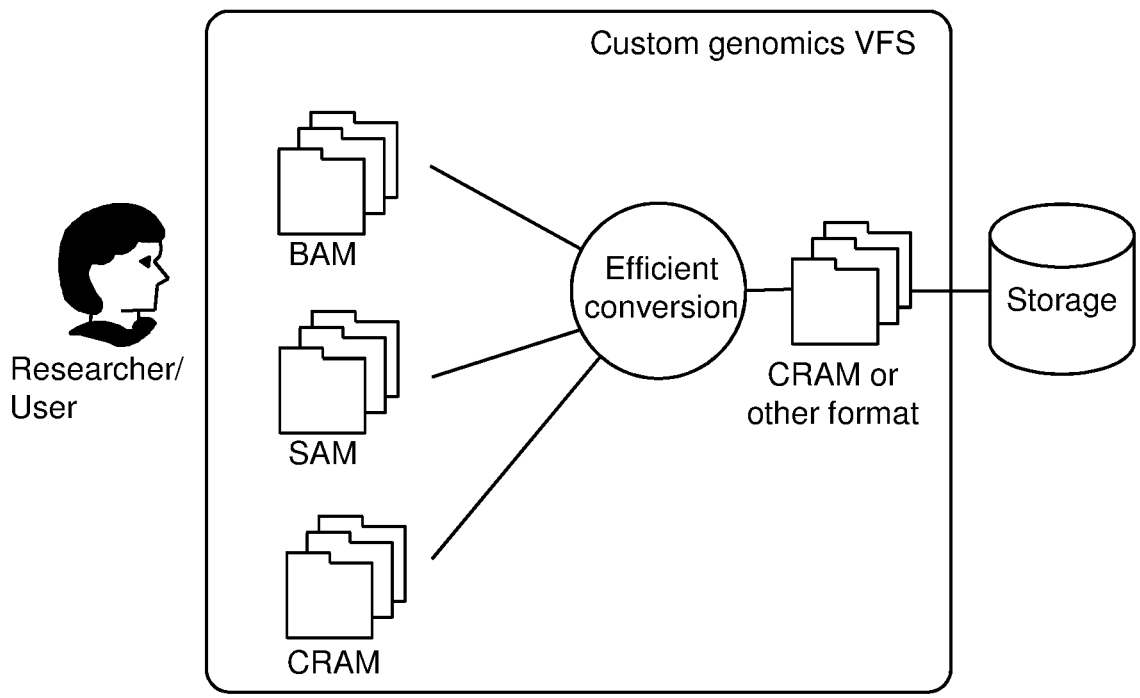
FIG. 1B is a schematic illustrating access to genomics data with a custom genomics Virtual File System.

Referring now to FIGS. 1A and 1B, shown is a schematic illustration of a difference between accessing genomics data in existing data storage systems and systems that utilise a custom genomics Virtual File System. FIG. 1A provides an illustration of how sequence files are directly saved in storage systems. FIG. 1B provides an illustration of the automatic conversion that happens upon access. This conversion occurs when storing the data, for example from BAM format, using efficient conversion to CRAM or other backend format. The inverse part of the conversion occurs when reading the same dataset.

Figure 2:
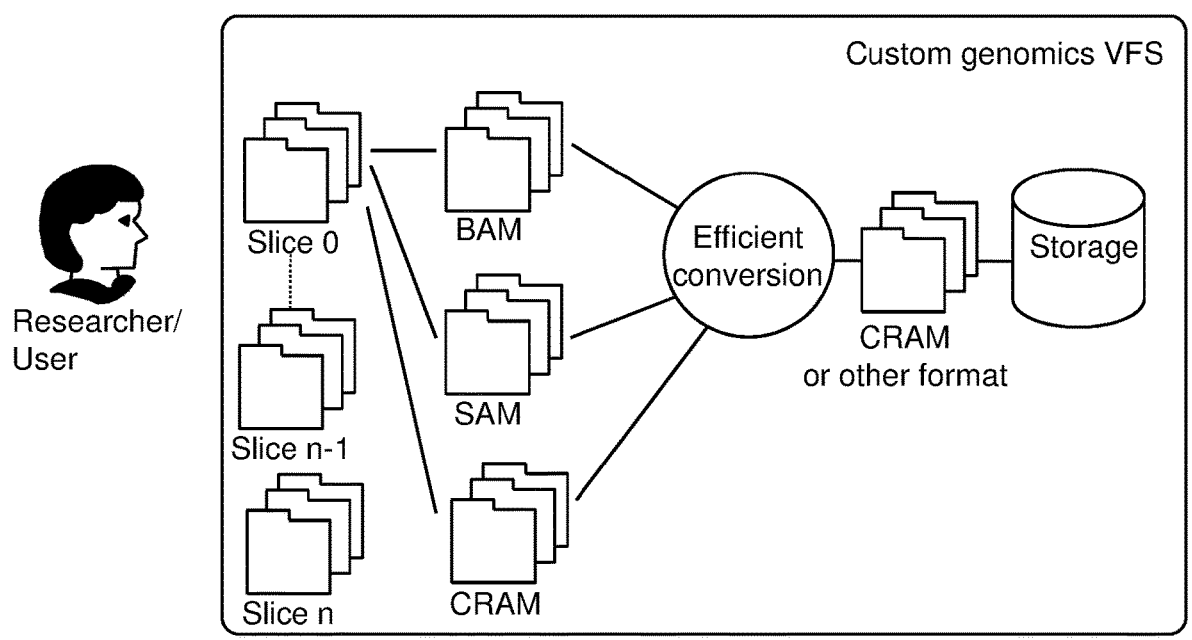
FIG. 2 is a schematic illustration of a representation of various views of slices (genome regions) on a custom genomics Virtual File System.

Referring now to FIG. 2, there is shown a schematic illustration of representation of various views of slices (genome regions) on a custom genomics Virtual File System. These advanced views represent specific regions of the genome and can be accessed in different data formats without any additional storage overheads.

Figure 3:
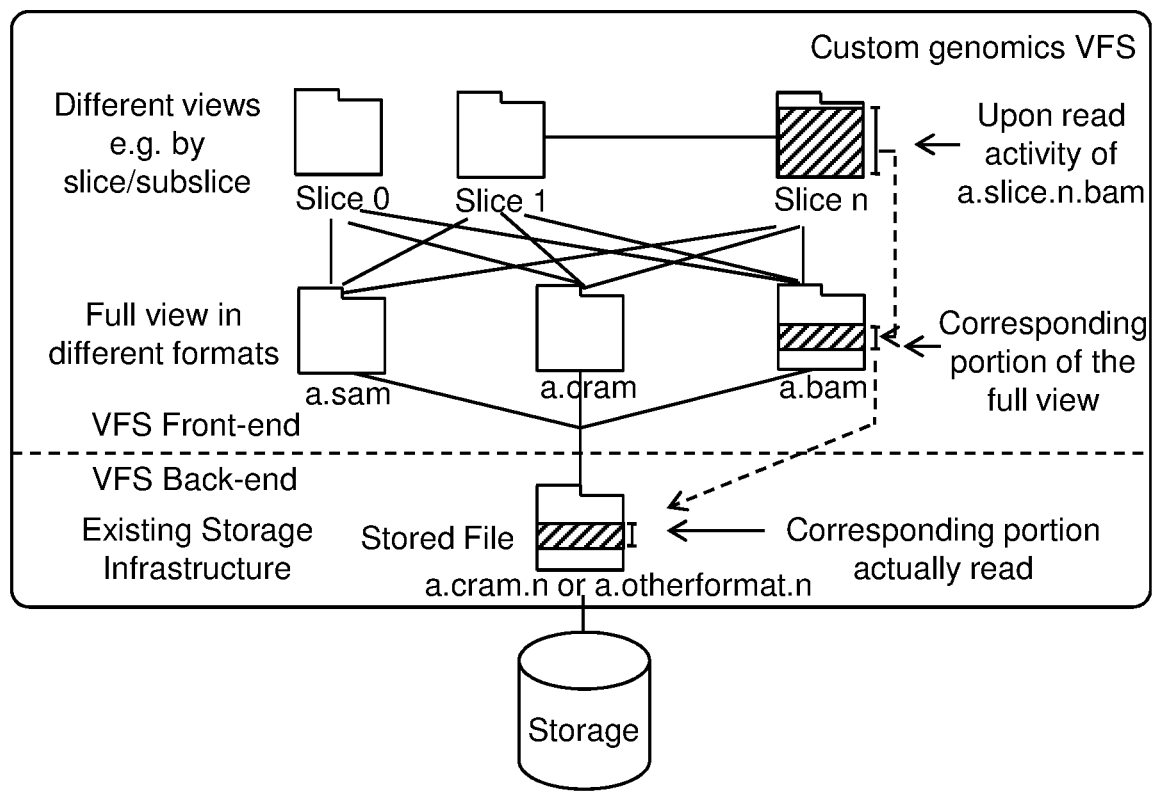
FIG. 3 is a schematic illustration of reading a sequence slice (genome region) as part of the Virtual File System.

Referring now to FIG. 3, there is shown a schematic illustration of reading a sequence slice (genome region) as part of the Virtual File System. Reading a specific region within the genome can be done efficiently by retrieving only the subset of the backend data that corresponds to the slice that is read. This is not affected by the format of the front end.

Figure 4:
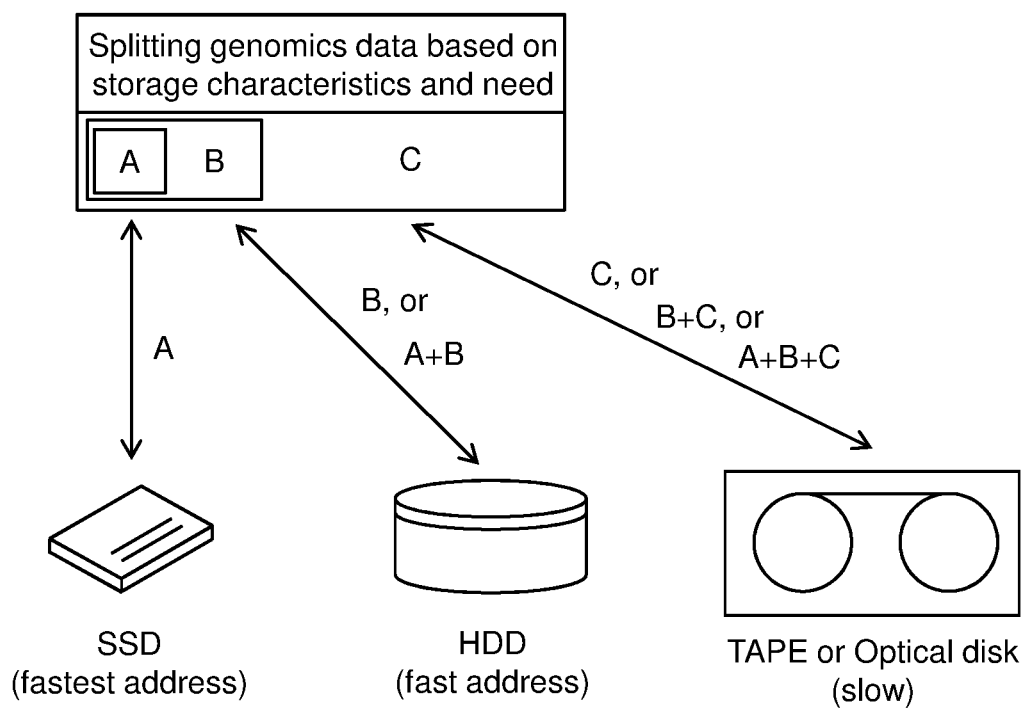
FIG. 4 is a schematic illustration of a method for splitting genomics data across a plurality of storage tiers, wherein the storage tiers are optionally mutually different.

Referring now to FIG. 4, there is shown a schematic illustration of steps of a method for splitting genomics data across different storage tiers. In FIG. 4, A represents the portion of the data that is accessed most frequently and is therefore stored in the storage module that has the fastest access (for example, SSD to reduce latency). B represents a larger portion of the data (excluding A). This data is typically characterised with lower frequency of access compared to A and may be too big (or expensive) to be stored in the fastest storage module. It is therefore moved to the next lower tier (for example, HDD). Finally, portion C is characterised with infrequent access (excluding A and B). This data is moved to the lowest performing tier since it also corresponds to the lowest costing tier. Portioning is either determined dynamically by frequency of access or is predetermined by type categories/tags. Alternatively, rather than splitting into exclusive parts, one can split with overlapping parts, so that B can include A, and C can include A and B. This alternative way of splitting allows for reading the required data present in that tier without needing another tier for reconstituting the data.

Referring now to FIG. 5, there is shown a schematic illustration of the method of writing on the VFS. In FIG. 5, a new BAM file named newfile.bam is being written to k different storage tiers. Each front-end data format includes a decoder and an encoder for the corresponding format. As newfile.bam data is being written to the VFS, the BAM decoder will convert it if necessary to the common data format. This process will then be followed by splitting the data. The data splitter will determine according to some preconfigured or a dynamic policy what storage tier it will be written to. It will be appreciated that the data splitter can choose to write the same block of data to multiple tiers. Data compression is also performed in the same stage. As the data is written, it may be optionally indexed for more efficient access. The index may also be written into one or multiple storage tiers.

Referring now to FIG. 6, there is shown a schematic illustration of the method of reading from the VFS. In this illustration a file named HG03052.BAM is being read from k different storage tiers. When data from HG03052.BAM is requested to be read from the VFS front-end, the location of data that corresponds to HG03052.BAM in the VFS backend is determined. If the data is split across multiple storage tiers, it is merged accordingly. Any decompression from the back-end format that may be required will also be performed at this point. If necessary, this data will be encoded in BAM format before the read request can be served by the VFS front-end.

Modifications to embodiments of the invention described in the foregoing are possible without departing from the scope of the invention as defined by the accompanying claims. Expressions such as "including", "comprising", "incorporating", "consisting of", "have", "is" used to describe and claim the present invention are intended to be construed in a non-exclusive manner, namely allowing for items, components or elements not explicitly described also to be present. Reference to the singular is also to be construed to relate to the plural. Numerals included within parentheses in the accompanying claims are intended to assist understanding of the claims and should not be construed in any way to limit subject matter claimed by these claims.

The invention claimed is:

1. A method of managing data representing genome sequence information, the method comprising:
    obtaining at least one file having a first format, the at least one file containing the data representing the genome sequence information, the data comprising tag fields;
    portioning the data in the at least one file into a plurality of data portions;
    assigning each of the plurality of data portions to one or more of a plurality of machine readable data storage media of a virtual file system;
    recording the plurality of data portions separately into the one or more of the plurality of machine readable data storage media in accordance with the assigning, in a second file format different from the first file format,
    wherein portioning the data in the at least one file into the plurality of data portions comprises
        splitting the tag fields into two or more of the plurality of data portions and
    wherein recording the plurality of data portions separately into the one or more of the plurality of machine readable data storage media in accordance with the assigning comprises:
        compressing the plurality of data portions by compressing at least some of the plurality of data portions using different compression algorithms, or
        storing a first of the two or more data portions in a first data storage medium of the plurality of machine readable data storage media and a second of the two or more data portions in a second data storage medium of the plurality of machine readable data storage media, wherein the first data storage medium is configured for faster access than the second data storage medium.

2. The method of claim 1, wherein the plurality of data portions includes a primary data portion and a secondary data portion, wherein the method includes accessing the secondary portion less frequently than the primary portion.

3. The method of claim 1, further comprising: assembling the data in the at least one file by reading the plurality of data portions from the one or more of the plurality of machine readable data storage media and assembling the data in the at least one file from the plurality of data portions.

4. The method of claim 1, wherein the data in the at least one file is in a single file, and wherein the portioning comprises portioning the data in the single file into the plurality of data portions.

5. The method of claim 1, wherein the data in the at least one file comprises data stored in BAM, SAM, or CRAM format.

6. The method of claim 1, further comprising:
    providing a user of the virtual file system with access to the at least one file having the first format.

7. The method of claim 1,
wherein the assigning comprises assigning at least some of the plurality of data portions to different media in the plurality of machine readable data storage media, and
wherein the recording comprises recording the at least some of the plurality of data portions in the different media.

8. The method of claim 1, wherein the data comprises quality score information, and wherein portioning the data comprises:
splitting the quality score information into the first data portion that comprises a lossy version of the quality score information and the second data portion that comprises a full version of the quality score information.

9. The method of claim 8, wherein the plurality of machine readable data storage media comprises a first data storage medium and a second data storage medium, wherein the first data storage medium is configured for faster access than the second data storage medium, and wherein the first data portion is stored in the first data storage medium and the second data portion is stored in the second data storage medium.

10. The method of claim 1, wherein the data comprises quality score information, and wherein portioning the data comprises: splitting the quality score information into a first data portion that comprises a lossy version of the quality score information and a second data portion comprises a delta version of the quality score information, wherein the method further comprises using the delta version of the quality score information together with the lossy version of the quality score information to restore the full version of the quality score information.

11. The method of claim 10, wherein the plurality of machine readable data storage media comprises a first data storage medium and a second data storage medium, wherein the first data storage medium is configured for faster access than the second data storage medium, and wherein the first data portion is stored in the first data storage medium and the second data portion is stored in the second data storage medium.

12. An apparatus, including:
a computing device; and
a non-transitory computer-readable storage medium having stored thereon computer-readable instructions that, when executed by the computing device, cause the computing device to perform a method comprising:
obtaining at least one file having a first format, the at least one file containing data representing genome sequence information, the data comprising tag fields;
portioning the data in the at least one file into a plurality of data portions;
assigning each of the plurality of data portions to one or more of a plurality of machine readable data storage media of a virtual file system;
recording the plurality of data portions separately into the one or more of the plurality of machine readable data storage media in accordance with the assigning, in a second file format different from the first file format,
wherein portioning the data in the at least one file into the plurality of data portions comprises
splitting the tag fields into two or more of the plurality of data portions,
and
wherein recording the plurality of data portions separately into the one or more of the plurality of machine readable data storage media in accordance with the assigning comprises:
compressing the plurality of data portions by compressing at least some of the plurality of data portions using different compression algorithms, or
storing a first of the two or more data portions in a first data storage medium of the plurality of machine readable data storage media and a second of the two or more data portions in a second data storage medium of the plurality of machine readable data storage media, wherein the first data storage medium is configured for faster access than the second data storage medium.

13. The apparatus of claim 12, wherein the data comprises quality score information and wherein portioning the data in the at least one file into the plurality of data portions comprises:
splitting the quality score information into a first data portion that comprises a lossy version of the quality score information and a second data portion that comprises a full version of the quality score information, or
splitting the quality score information into a first data portion that comprises a lossy version of the quality score information and a second data portion comprises a delta version of the quality score information, wherein the method further comprises using the delta version of the quality score information together with the lossy version of the quality score information to restore the full version of the quality score information.

14. A non-transitory computer-readable storage medium storing computer-readable instructions that, when executed by a computing device, cause the computing device to perform:
obtaining at least one file having a first format, the at least one file containing data representing genome sequence information, the data comprising tag fields;
portioning the data in the at least one file into a plurality of data portions
assigning each of the plurality of data portions to one or more of a plurality of machine readable data storage media of a virtual file system;
recording the plurality of data portions separately into the one or more of the plurality of machine readable data storage media in accordance with the assigning, in a second file format different from the first file format,
wherein portioning the data in the at least one file into the plurality of data portions comprises
splitting the tag fields into two or more of the plurality of data portions,
and
wherein recording the plurality of data portions separately into the one or more of the plurality of machine readable data storage media in accordance with the assigning comprises:
compressing the plurality of data portions by compressing at least some of the plurality of data portions using different compression algorithms, or
storing a first of the two or more data portions in a first data storage medium of the plurality of machine readable data storage media and a second of the two or more data portions in a second data storage medium of the plurality of machine readable data storage media, wherein the first data storage medium is configured for faster access than the second data storage medium.

15. The non-transitory computer-readable storage medium of claim 14, wherein the data comprises quality score information and wherein portioning the data in the at least one file into the plurality of data portions comprises:

splitting the quality score information into a first data portion that comprises a lossy version of the quality score information and a second data portion that comprises a full version of the quality score information, or splitting the quality score information into a first data portion that comprises a lossy version of the quality score information and a second data portion comprises a delta version of the quality score information, wherein the method further comprises using the delta version of the quality score information together with the lossy version of the quality score information to restore the full version of the quality score information.

\* \* \* \* \*